United States Patent
Han et al.

(10) Patent No.: US 7,136,760 B2
(45) Date of Patent: Nov. 14, 2006

(54) VISUALIZATION METHOD OF RNA PSEUDOKNOT STRUCTURES

(75) Inventors: Kyungsook Han, 303-2003, Hyundai-3rd Apt., Ongnyeon-dong, Yeonsu-ku, Incheon 406-772 (KR); Wootaek Kim, Pohang-si (KR); Yujin Lee, Seoul (KR); Hong-Jin Kim, Yeonsu-ku (KR)

(73) Assignee: Kyungsook Han (KR)

( * ) Notice: Subject to any disclaimer, the term of this patent is extended or adjusted under 35 U.S.C. 154(b) by 421 days.

(21) Appl. No.: 10/170,251

(22) Filed: Jun. 11, 2002

(65) Prior Publication Data

US 2003/0176992 A1    Sep. 18, 2003

(30) Foreign Application Priority Data

Jan. 29, 2002   (KR) ................... 2002-5192

(51) Int. Cl.
   *G06F 7/00*    (2006.01)
   *G01N 33/48*   (2006.01)
   *C12Q 1/68*    (2006.01)
   *G06G 7/48*    (2006.01)

(52) U.S. Cl. ............... 702/20; 702/19; 703/11; 435/6; 707/102

(58) Field of Classification Search ............ 702/19–20; 707/102; 703/11; 435/6; 536/23.1
   See application file for complete search history.

(56) References Cited

OTHER PUBLICATIONS

'A vector-based method for drawing RNA secondary structurez', by Kyungsook Han, Dohyung Kim and Hong-lim Kim, Bioinformatics, vol. 15, No. 4, pp. 286-297 (1999).*

Rnaviz, a program for the visualization of RNA secondary structure, by Peter De Rijk and Rupert De Wachter, Nucelic Acids Research, vol. 25, No. 22, pp. 4679-4684 (1997).*

New Developments in Structure Determination of Pseudoknots, Cornelis W. Hilbers, Paul J.A. Michiels, Hans A. Heus, Biopolymers (Nucleic Acid Sciences), vol. 48, pp. 137-153 (1998).*

PseudoBase: structuraz information on RNA pseudoknotst, F.H.D. van Batenburg, A.P. Gutyaev and C.W.A. Pleij, Nucleic Acids Research, vol. 29, No. 1, pp. 194-195 (2001).*

"Pseudoviewer", available at http://pseudoviewer.inha.ac.kr as provided by a web intelligence laboratory at Inha University, 253 Younghyun-dong, Nam-gu Incheon, 402-751.*

* cited by examiner

*Primary Examiner*—Mark K. Zeman
(74) *Attorney, Agent, or Firm*—Bachman & LaPointe, P.C.

(57) ABSTRACT

Disclosed is a visualization method of RNA pseudoknot structures. The method of the invention comprises the steps of setting criteria required for visualizing RNA pseudoknots, setting structural elements and data structures for representing a whole RNA structure containing pseudoknots, determining an input format for visualization and a drawing order of the structure, determining connectivity relations between regular loops and stems in the structure and between pseudoknot loops and stems in the structure, calculating radii of the regular loop and the PK loop, calculating coordinates of bases in the regular loops, setting internal angles of the PK loops, calculating startAngles of the regular loops and angles of the stem, determining positions of the pseudoknots in the PK loops, and drawing the pseudoknots and the whole RNA structure containing the pseudoknots.

17 Claims, 13 Drawing Sheets
(10 of 13 Drawing Sheet(s) Filed in Color)

US 7,136,760 B2

VISUALIZATION METHOD OF RNA PSEUDOKNOT STRUCTURES

BACKGROUND OF THE INVENTION

1. Field of the Invention

The present invention relates to a new representation method of RNA pseudoknot structures and a visualization method of the RNA pseudoknot structures and a whole RNA structure containing the pseudoknots, and more particularly to a visualization method of RNA pseudoknot structures for the prediction and modeling thereof.

2. Description of the Related Art

A pseudoknot structure in a RNA molecule is a tertiary structural element formed when bases in a loop of secondary structure pair with complementary bases outside the loop. RNA pseudoknots are not only an essential structural element to form tertiary structures of RNA, but also are responsible for important functions of RNA.

Although several computer programs for visualizing a secondary structure of RNA are available (for example, those disclosed by De Rijk & De Wachter, 1997 and Han et al., 1999), there are no automated techniques or programs for visualizing a RNA pseudoknot structure. In the sense of graph theory, a drawing of RNA secondary structure is a tree, whereas a drawing of RNA pseudoknot structure is a graph. Thus, drawing RNA pseudoknot structures requires many more computations to visualize, compared to RNA secondary structures.

Currently, RNA pseudoknots are represented by drawing RNA secondary structures first, using a visualizing program of RNA secondary structures, and then either adding line segments to the secondary structure drawings or modifying the RNA secondary structure drawings with the aid of a graph-editing function. Such a drawing relying on a significant amount of manual work for visualization is difficult and yields an unsatisfactory result, as a whole RNA size increases.

FIGS. 1a to 1d display conventional representations of H-type pseudoknots of RNA (Hilbers et al., 1998). FIG. 1a is a general configuration for representing a pseudoknot structure in which dotted lines indicate base pairings between bases in a hairpin loop and bases in the 3' direction of the RNA sequence. FIGS. 1b to 1d represent pseudoknot structures obtained by eliminating one of three loops from the pseudoknot structure of FIG. 1a, and by stacking stem 1 and stem 2 coaxially, thereby mimicking a single stem in the representation. In particular, FIGS. 1b to 1d can be obtained from FIG. 1(a) by eliminating loop 1, loop 2 and loop 3, respectively. The pseudoknot structure of FIG. 1(c) is the most abundant among natural RNAs.

However, the conventional method for the representation of pseudoknots has a disadvantage in that there are many edge crossings in the representation, thus being difficult to follow RNA sequences from a 5'-end to a 3'-end, so making it hard to easily recognize the pseudoknot structures.

SUMMARY OF THE INVENTION

Therefore, the present invention has been made in view of the above problem and the inventors present a new representation method of H-type pseudoknot structures, and it is an object of the present invention to provide a visualization method of an RNA structure containing H-type pseudoknots, on the basis of the new representation method, thereby producing a clear and more aesthetically pleasing drawing.

BRIEF DESCRIPTION OF THE DRAWINGS

The patent or application file contains at least one drawing executed in color. Copies of this patent or patent application publication with color drawing(s) will be provided by the Patent & Trademark Office upon request and payment of the necessary fee.

The above and other objects, features and other advantages of the present invention will be more clearly understood from the following detailed description taken in conjunction with the accompanying drawings, in which.

DESCRIPTION OF THE PREFERRED EMBODIMENTS

The present invention is accomplished by the provision of a visualization method of RNA pseudoknot structures, the method comprising the steps of:

(a) setting criteria required for visualizing RNA pseudoknots;

(b) setting structural elements and data structures for representing a whole RNA structure containing pseudoknots;

(c) determining an input format for visualization and a drawing order of the structure;

(d) determining connectivity relations between regular loops and stems in the structure and between pseudoknot loops (PK loops) and stems in the structure;

(e) calculating radii of the regular loops and the PK loops;

(f) calculating coordinates of bases in the regular loops;

(g) setting internal angles of the PK loops;

(h) calculating startAngles of the regular loops and angles of the stems;

(i) determining positions of the pseudoknots in the PK loops; and, (j) drawing the pseudoknots and the whole RNA structure containing the pseudoknots.

Figure 1:
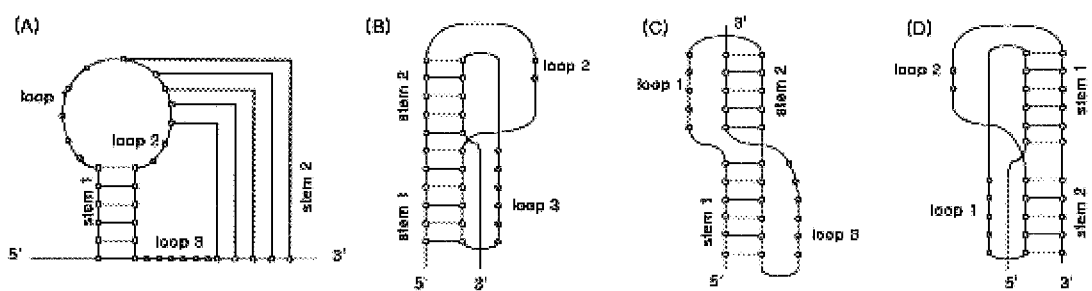
FIGS. 1a to 1d are drawings showing conventional representations of H-type pseudoknot structures.
Figure 2:
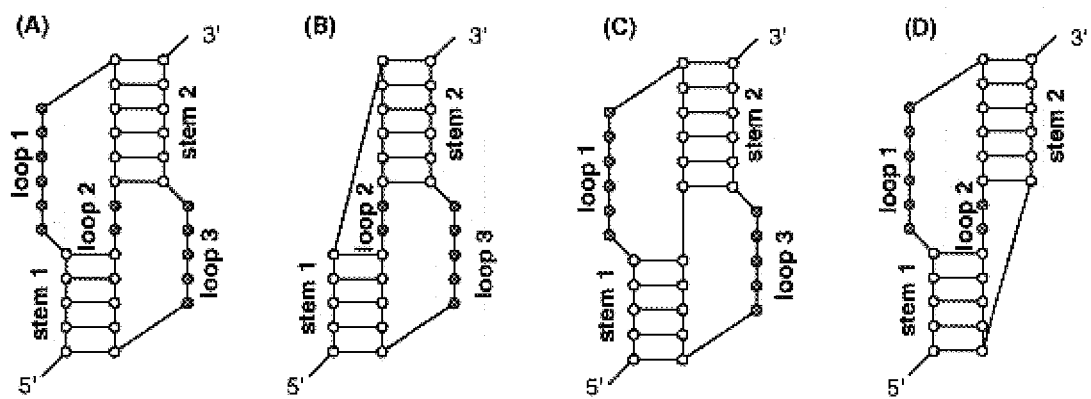
FIGS. 2a to 2d are drawings showing new representations of H-type pseudoknot structures.
Figure 3:
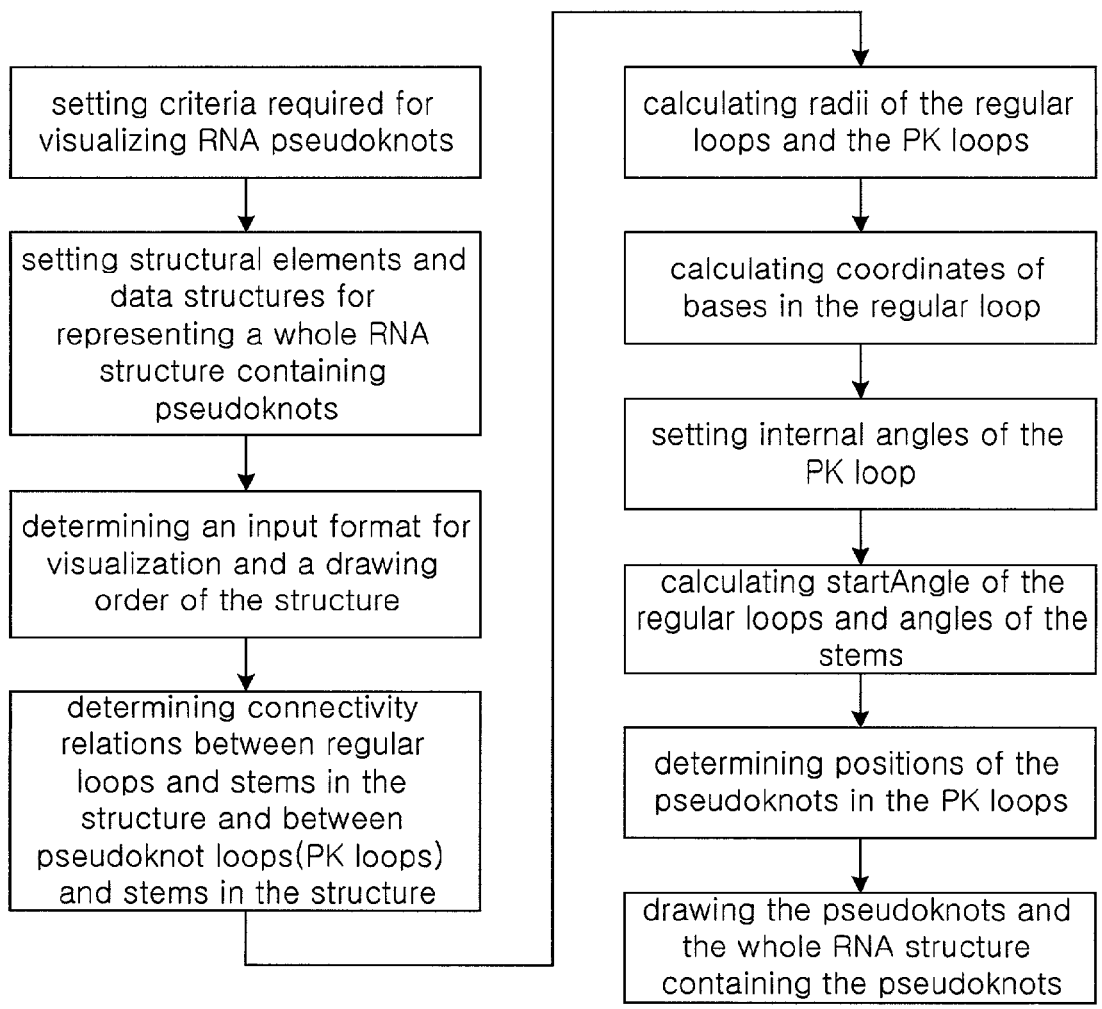
FIG. 3 is a flow chart illustrating a program for visualizing RNA pseudoknot structures.

The visualization method of RNA pseudoknot structures of the invention is described step by step in detail with reference to the accompaning drawings, especially FIG. 3 (a flow chart of the visualization program).

For RNA pseudoknot structures, new representations according to the invention are shown in FIGS. 2a to 2d. FIGS. 2a to 2d correspond to FIGS. 1a to 1d, respectively.

In accordance with the invention, criteria and data structures for the visualization of RNA pseudoknot structures are employed. Two criteria for visualizing RNA pseudoknot structures are adopted in designing the algorithm for PseudoViewer, the program of the invention: (1) overlapping of structural elements should be minimized to maximize the readability of the drawing visualizing pseudoknot structures; (2) not only pseudoknots themselves but also the whole RNA structure containing the pseudoknots should be visualized to be quickly and easily recognizable.

In the invention, the visualization of RNA pseudoknot structures is achieved by taking structural elements into consideration, because the drawing for the visualization includes the whole structure containing the pseudoknots, not only the pseudoknot regions. The structural elements include a stem, a regular loop, a pseudoknot and a pseudoknot loop. The stem or helix is a double stranded part, containing two or more consecutive base pairs. The regular loop is a single stranded part, containing non-pairing bases. It includes hairpin loops, bulge loops, internal loops, multiple loops and dangling ends. The dangling end is not a real loop though it has a single stranded part. In the invention, these loops are considered as regular loops for convenience. The pseudoknot is a tertiary structural element which is formed by pairing of bases in a regular loop with complementary bases outside the loop. The pseudoknot loop is a loop containing another single stranded part as well as a pseudoknot.

The program, PseudoViewer has respective classes for structural elements. The PseudoViewer also has a "Pseudoknot" class as a separate class. Each class has data members called "baseVectors". BaseVectors are variables of vector type, associated with respective bases in each class. In this program, baseVectors of the "Pseudoknot loop" class include objects of the Pseudoknot class. The following Table 1 shows a data structure for the "Base" class.

TABLE 1

| Data Type | Variable | Description |
|---|---|---|
| double | X | x coordinate of a base |
| double | Y | y coordinate of a base |
| double | Angle | An angle between a base and a starting base of Rloop |
| int | BaseNum | A number indicating the position of a base in a sequence |
| int | Agcu | One among A, G, C and U |
| Int | Pair | One among :, [, ], (, and) |
| Int | pairBase | A number indicating the position of a base which pairs with another base in a stem; if such a base does not exist, the value is −1. |
| Boolean | hasloop | If a next base is a starting base in a loop, then true is assigned. |
| Boolean | hasPair | If a base has a complementary base to pair in a stem, then true is assigned. |
| Boolean | isLeftSide | If a base is positioned on the left, then true is assigned; in the case of a base in a loop, not be determined (This variable is determined only in the case of bases in a stem within a pseudoknot). |
| Boolean | isstemStart | If a current base is a starting base in a stem, then true is assigned. |
| Boolean | isstemEnd | If a base is an ending base in a stem, then true is assigned. |
| Boolean | isloopStart | If a base is a starting base in a loop, then true is assigned. |
| Boolean | isloopEnd | If a base is an ending base in a loop, then true is assigned. |
| Boolean | isPKStart | If a base is a starting base in a pseudoknot, then true is assigned. |
| Boolean | isPKEnd | If a base is an ending base in a pseudoknot, then true is assigned. |
| Boolean | isInSloop | If a base is already contained in R loop, then true is assigned (This variable is employed in calculating a size of a R loop) |
| Boolean | isInPK | If a base is in a pseudoknot, then true is assigned. |
| Boolean | isInstem | If a base is in a stem, then true is assigned. |
| Boolean | isRloopStart | If a base is a starting base in a R loop, then true is assigned. |
| Boolean | isRloopEnd | If a base is an ending base in a R loop, then true is assigned. |
| Boolean | isInPKloop | If a base is in a PK loop, then true is assigned. |

Figure 4:
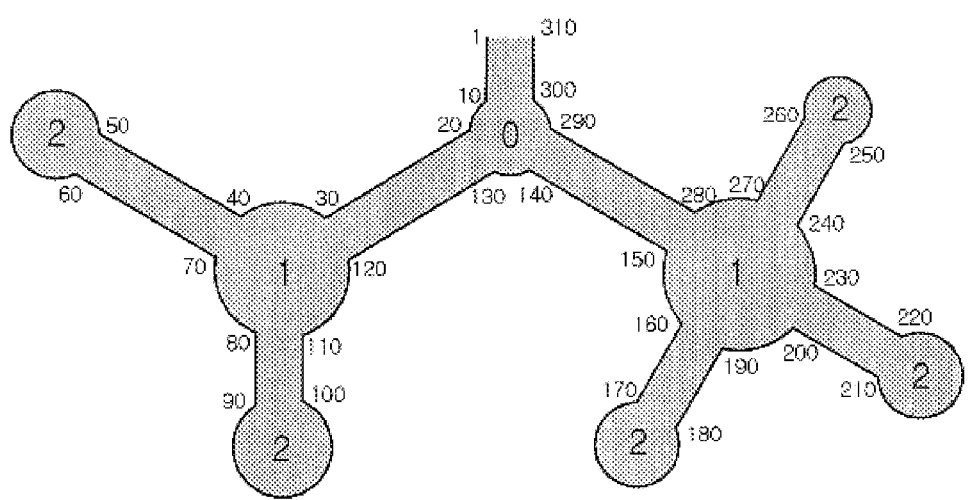
FIG. 4 is a drawing showing an abstract tree for representing regular loops and pseudoknot loops.

The class of regular loops has data members "rloopDepth". These data members rloopDepth are variables representing respective depths of nodes in a tree structure of regular loops. The nodes correspond to respective regular loops in the tree structure. The numeral in each node of FIG. 4 indicates a rloopDepth value, denoting a level or a depth of the corresponding loop, and the numerals outside each stem indicate starting base numbers and ending base numbers of the stem, respectively. For example, the numbers "1", "10", "300" and 310 " outside the stem positioned on the node of the level 0 denote that the stem is formed by base pairing between bases 1~10 and bases 300~310.

In the tree structure mentioned above, where a regular loop has a lower starting base number and a higher ending base number than those of a current loop, it is determined to be an upper regular loop (that is, its rloopDepth value is lower). Whenever such a regular loop meeting the above condition is found, an increment in rloopDepth value is made. Thus, respective rloopDepth values of lower nodes can be calculated. In drawing regular loops, loops and stems connected thereto are drawn in the order of levels, according to the calculated rloopDepth values.

The notations used herein, unless specified otherwise, are as follows.

1. All angles are measured with respect to a positive y-axis.

2. Unit of angles is radian rather than degree.

3. Modulo operator (%) is applied for calculating angle values. That is, angle values are in the range of [0, 2Π].

4. In the drawing, red-filled circles represent the bases in a single stranded part, that is, non-pairing bases, while empty circles represent the bases in a stem, that is, pairing bases.

Next, the input format for the visualization of RNA Pseudoknots and the drawing sequence according to the present invention will be described.

According to the invention, PseudoViewer takes as its input an ASCII file to represent pseudoknots and secondary structures of RNA molecules in the form of a pairing format. This format is also used in another program PseudoBase for representing pseudoknots.

One of input data is exemplified as below. In this example, a pseudoknot is formed by base pairing $G_{56}CGGUU_{61}$ with $A_{74}GCCGC_{79}$.

```
                                            (SEQ ID NO 1)
    50       60       70
CGA GGGG CGGU UGG CCU CGU AAAAA GCCGC
%(((((:[[[[[::)))))::::::]]]]]
```

This input data represents a pseudoknot structure including bases respectively denoted by specific ASCII codes, that is, round brackets, square brackets, and, colons. The bases denoted by the round or square brackets form a stem while being arranged in pairs. One base of each base pair in the stem is denoted by an open bracket, whereas the other base of the base pair is denoted by a closed bracket. The bases denoted by the colons form a loop or loops while being present in a non-paired state.

Based on the input data, PseudoViewer draws a pseudoknot. PseudoViewer first sets a starting point to draw the pseudoknot structure based on the input data. That is, the coordinates of the starting point are determined to be "(1, 1)". Once the coordinates of the starting point are set, the position of the base corresponding to the last one of the closed round brackets is determined by an x-coordinate value increased from the x-coordinate value of the starting point by a value corresponding to a stem width, and a y-coordinate value corresponding to the y-coordinate value of the starting point. Thereafter, respective positions of the remaining closed round bracket bases are determined in a reverse order by y-coordinate values sequentially incremented from the y-coordinate value of the starting point by the value corresponding to the stem width, and x-coordinate values each corresponding to the x-coordinate value of the last closed round bracket base. That is, the closed round bracket bases are aligned together along a central line extending in a y-axis direction while being spaced from the start point in an x-axis direction by the stem width. Respective positions of bases corresponding to the open round brackets are also determined in a normal order by y-coordinate values respectively corresponding to the y-coordinate values of the closed round bracket bases paired therewith, and x-coordinate values each corresponding to the x-coordinate value of the starting point. Accordingly, the open round bracket bases are aligned along a line extending in a y-axis direction through the starting point in parallel to the central line. Where there are open square brackets between the open round brackets and the closed round brackets, respective positions of bases preceding the closed round brackets are determined in a reverse order by y-coordinate values sequentially incremented from the y-coordinate value of the first one of the closed round bracket bases by the value corresponding to the stem width and x-coordinate values each corresponding to the x-coordinate value of the first closed round bracket base, until the position determination for the first one of the open square brackets is completed. Accordingly, the bases preceding the closed round bracket bases are aligned together along the central line. Where there are non-paired bases between the open round bracket bases and the open square brackets, respective positions of the non-paired bases are determined in a normal order by y-coordinate values sequentially incremented from the y-coordinate value of the last one of the open round bracket bases by the value corresponding to the stem width, and an x-coordinate value reduced from the x-coordinate value of the starting point by the value corresponding to the stem width. That is, the bases between the open square bracket base and the closed round bracket base are aligned together along a line extending in a y-axis direction while being spaced apart from the y-axis line extending through the start line, by the stem width. Subsequently, respective positions of bases corresponding to the closed square brackets are determined in a normal order by y-coordinate values respectively corresponding to the y-coordinate values of the open square bracket bases paired therewith, and x-coordinate values respectively reduced from the x-coordinate values of the open square bracket bases. Where there are non-paired bases between the closed round bracket bases and the closed square bracket bases, respective positions of the non-paired bases preceding the closed square brackets are determined in a reverse order by y-coordinate values sequentially decremented from the y-coordinate value of the first one of the closed round bracket bases by the value corresponding to the stem width, and an x-coordinate value increased from the x-coordinate value of the first closed square bracket base by the value corresponding to the stem width. That is, the non-paired bases preceding the closed square brackets are aligned together along a line extending in a y-axis direction while being spaced from the central line by a distance double the stem width. Thus, the stems of the pseudoknot structure are arranged at opposite sides of the central line, respectively, in such a fashion that their opposite bases are aligned along the central line. Also, each loop is arranged at the left or right side of the central line. The arrangement of the loop is determined, based on the position-determined base to which the loop is connected.

Figure 5:
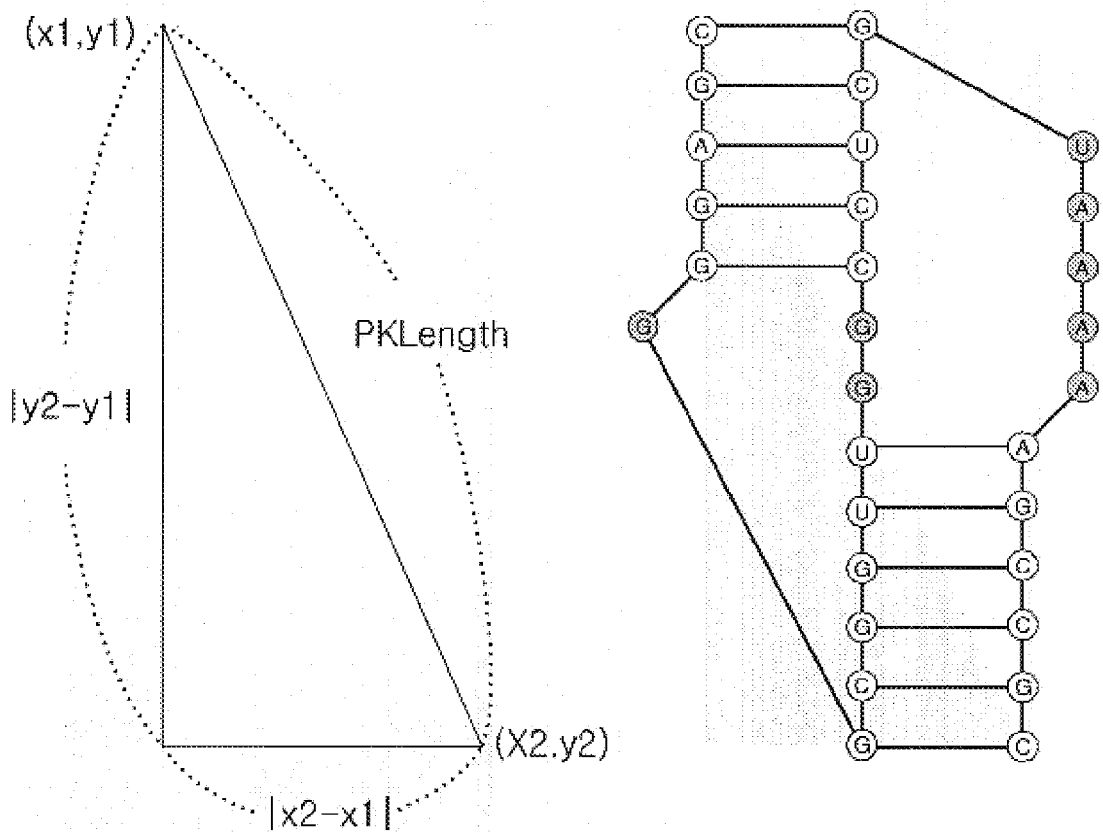
FIG. 5 is a drawing representing a pseudoknot structure.

The above input data can be visualized, as in FIG. 5. The PKLength, a data member of the class Pseudoknot, denotes the diagonal length of a bounding box of the pseudoknot and is calculated using Equation 1.

$$PKLength = \sqrt{(x_{max} - x_{min})^2 + (y_{max} - y_{min})^2} \qquad \text{[Equation 1]}$$

wherein:

$x_{min}$ and $y_{min}$ represent, respectively, x and y coordinates of the starting base of a pseudoknot; and, $x_{max}$, and $y_{max}$ represent, respectively, x and y coordinates of the ending base of a pseudoknot.

Figure 6:
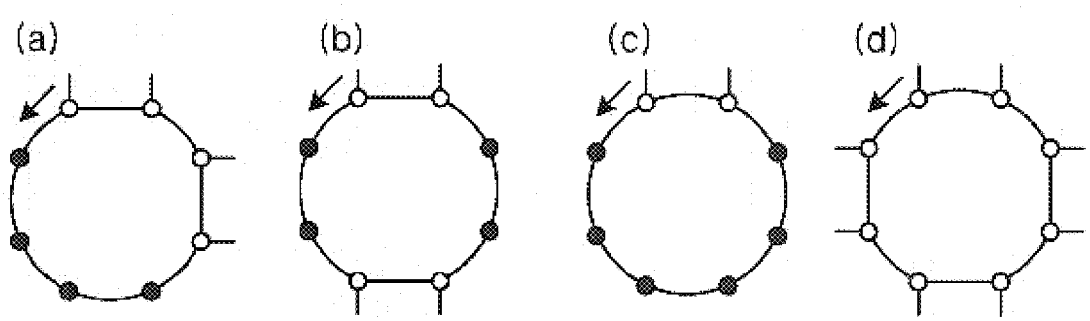
FIGS. 6a to 6d are drawings showing connectivity relations between regular loops and stems.

FIGS. 6a to 6d are intended to show diverse connecting structures of stems to a regular loop, respectively. There can be 4 types of connecting structures. Each arrow in FIGS. 6a to 6d represents a proceeding direction in terms of bases in the regular loop. FIG. 6a is the structure in which there is no intervening base between two stems. That is, one stem is directly adjacent to the other stem. FIG. 6b is the structure in which at least one intervening base is between two stems. FIG. 6c is the structure in which only one stem is connected to a regular loop. FIG. 6d is the structure in which all stems connected to the regular loop are directly adjacent, with no intervening base between stems.

The bases of each stem in a pseudoknot structure can be determined as follows. That is, it is first determined whether or not the current base is the last one of bases included in the stem. This determination is repeated for all bases in the pseudoknot structure until the last base of the stem is determined. The determination of the last base can be achieved, based on a variable "isstemEnd" in the Base class. The regular loop of the pseudoknot structure starts from the determined last base of the stem. The regular loop is ranged between the last base of the stem and the base of the stem paired therewith. In order to determine which bases are included in the regular loop, it is needed to check whether or not the current base has a non-pair value represented by ":", as the value of its variable "pair". Where the variable pair value of the current base does not correspond to the non-pair value represented by ":", it is determined that the current base is a base of the regular loop. This checking is repeated for all bases in the pseudoknot structure until the last base of the regular loop is determined. It should be noted that where the pseudoknot structure has a plurality of stems, the same regular loop may be searched several times because such a regular loop search is carried out whenever a search of one stem is completed. As for an algorithm for representing an entire RNA structure, it is also noted that bases in a pseudoknot loop should not be subjected to such a search, since the program considers a pseudoknot loop as a regular loop.

Thus, a regular loop should be searched to find a starting base of the regular loop only when "false" is assigned with regard to both values of isInRloop (is it already contained in a regular loop?) and isInPKloop (is it contained in a Pk loop?).

Figure 7:
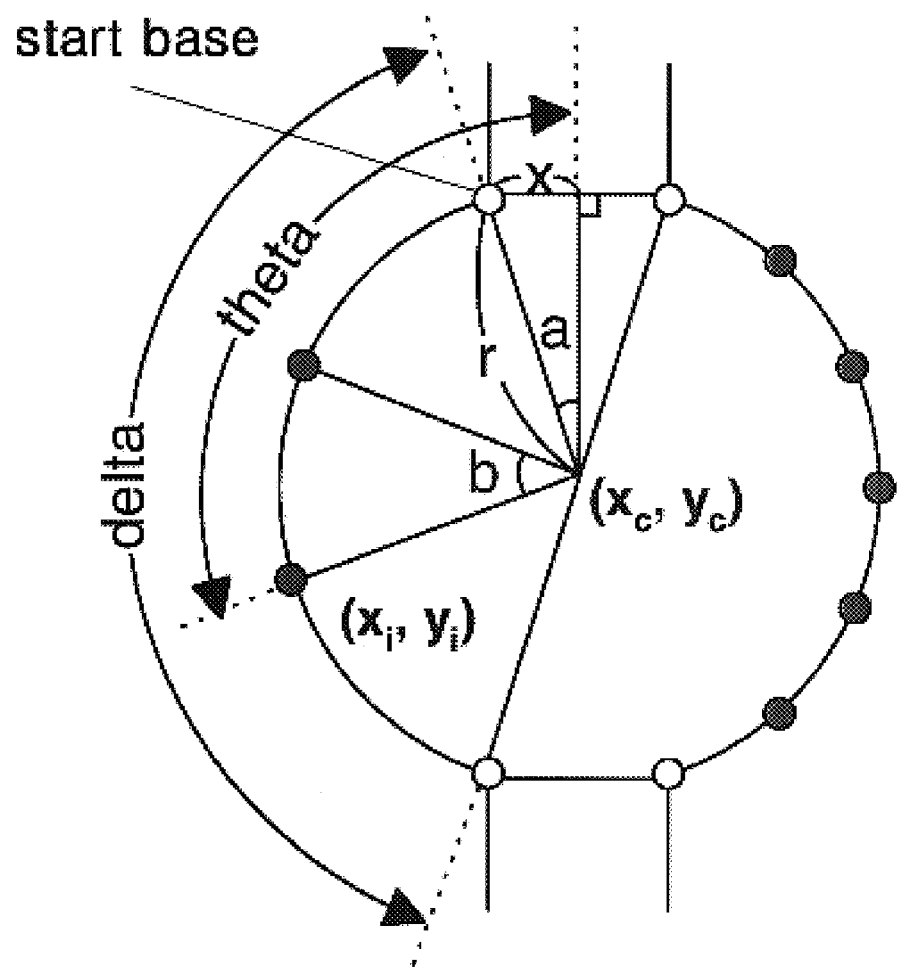
FIG. 7 is a drawing showing a radius of a regular loop and positions of bases therein.

The outline of a regular loop is drawn in a circle shape on which tiny circles are settled, the tiny circles indicating bases. The radius of the circle can be determined. When the distance between the centers of adjacent bases in the regular loop is 2x, the regular loop is represented as in FIG. 7. In FIG. 7, empty tiny circles indicate bases in stems, while red tiny circles indicate unpaired bases.

As shown in FIG. 7, it is seen that the regular loop consists of n isosceles triangles, and the width of stem is 2x (x is half of the width). Given that the distance between adjacent bases is the same, all isosceles triangles have the same size. Thus, the vertical angle a in FIG. 7 can be calculated using Equation 2 below.

$$a = \frac{2\pi}{2n} = \frac{\pi}{n} \qquad \text{[Equation 2]}$$

The radius r of the regular loop can be calculated using Equation 3.

$$r = \frac{x}{\sin a} \qquad \text{[Equation 3]}$$

Figure 8:
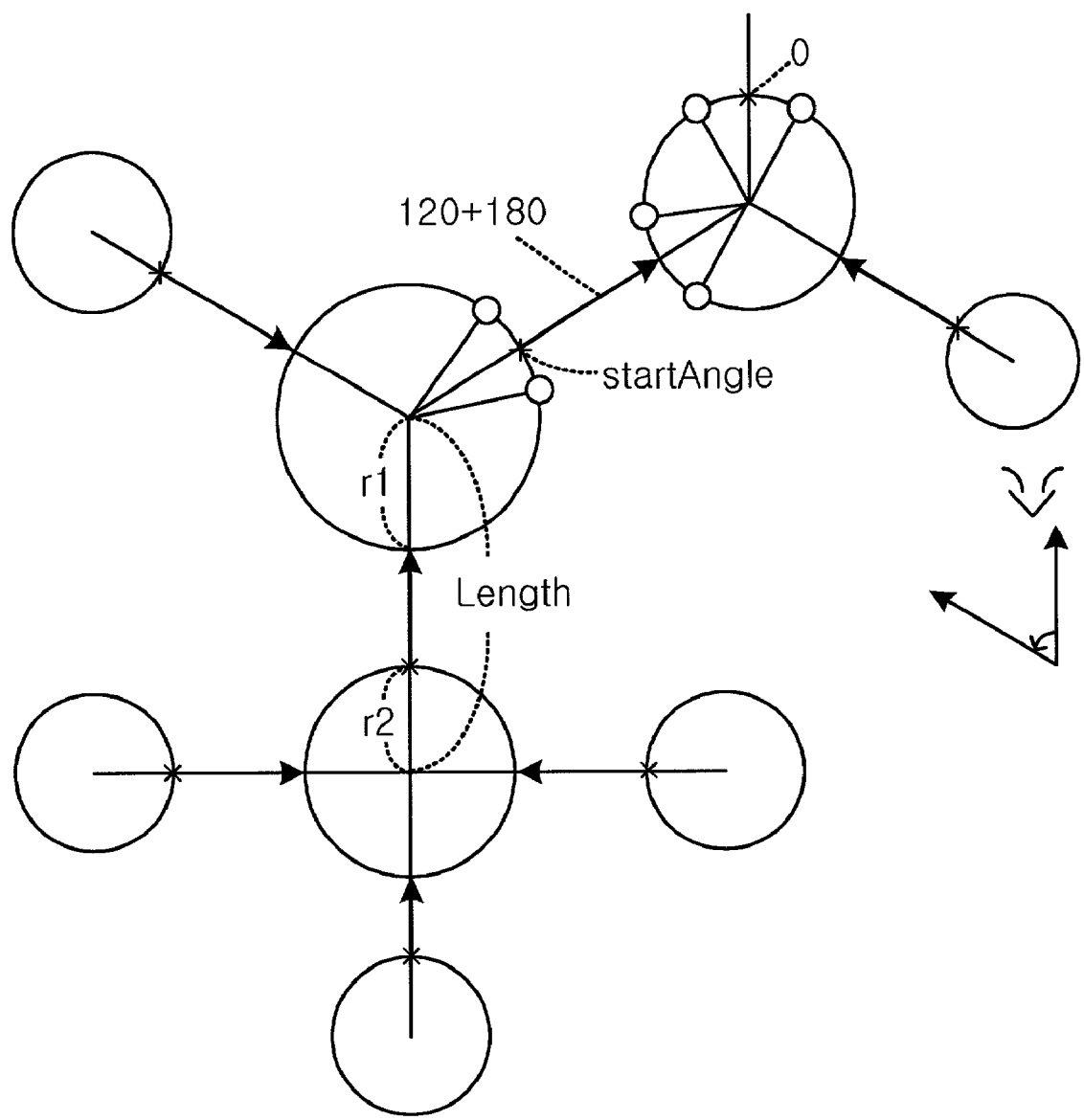
FIG. 8 is a drawing showing an angle of a stem in a regular loop, a startAngle and a distance between the centers of regular loops.

Positions of bases in the regular loop, not in a pseudoknot loop, are determined according to the number of bases. The positions of bases and the radius in the regular loop are shown in FIG. 8. In the outline, a straight line is drawn between the starting base in the stem and the base pairing therewith, and at the center of the line, another straight line is drawn perpendicular to the former line, the latter line being on a y-axis. The center of the regular loop is coincident with the center of xy coordinate chart. Providing that the number of intervening bases between adjacent stems which are connected to the regular loop is $n_b$, the angle δ between adjacent stems can be calculated using Equation 4.

$$\delta = 2a(n_b+2) \qquad \text{[Equation 4]}$$

An angle θ between the $i^{th}$ base and the positive y-axis can be calculated using the equation $\theta_i=(2i+1)a$, i=0, 1, 2, ..., n−1. The positions of bases are determined as coordinate values using the r value, the centric coordinates, and each angle of bases with respect to the y-axis. The coordinate values can be calculated using Equation 5.

$$x_i = -r \sin \theta_i + x_c$$

$$y_i = r \cos \theta_i + y_c \qquad \text{[Equation 5]}$$

wherein:

$x_i$ and $y_i$ represent, respectively, x and y coordinates of the $i^{th}$ base of the regular loop;

$x_c$ and $y_c$ represent, respectively, x and y coordinates of the center of the regular loop;

$\theta_i$ represents an angle between the $i^{th}$ base of the regular loop and the positive y-axis; and, r represents the radius of the regular loop.

The startAngle and stem angles of the regular loop can be determined. In FIG. 8, the arrows each indicate a direction from the stem to the lower-numbered bases. All angles are measured counter-clockwise, with respect to a positive y-axis.

For the regular loop with the loop level 0, both the angle of the first stem and the startAngle of the loop are zero. The stem angles Φ (stemAngle) of other stems are calculated using Equation 6. Notice that, in Equation 6, Π is added to make the stem having low-numbered bases point toward the upper regular loop, provided that the stem is parallel to the y-axis, and the bases in the stem are lower-numbered as the y coordinate value increases. A separate calculation for the startAngle of the lower regular loop is not required because it is the same as the angle of a current stem.

$$\Phi = D_{loop} + \pi + \delta \qquad \text{[Equation 6]}$$

wherein:

$D_{loop}$ represents the startAngle of the upper regular loop; and,

δ represents an angle between adjacent stems in the regular loop (calculated according to Equation 4).

The distance between regular loops can be determined as the distance between the centers of two circles representing the regular loops. It is a sum of the radius of the current regular loop, the length of the upper stem, and the radius of the upper regular loop. Meanwhile, the stem length is obtained by multiplying the number of base pairs in the stem by a certain value (stemHeight). The distance $D_{rl}$ between the centers of regular loops can be calculated using Equation 7 below.

$$D_{rl} = r_c + (n_{ub}-1) \times h_s + r_u \qquad \text{[Equation 7]}$$

wherein:

$r_c$ represents the radius of the current regular loop;

$r_u$ represents the radius of the upper regular loop;

$n_{ub}$ represents the number of base pairs of the upper stem; and, $h_s$ represents the distance between adjacent base pairs of the stem.

The entire loop containing pseudoknots is called herein a "pseudoknot loop" (PK loop). In determining the entire PK loop structure, the PK loop is considered as a regular loop. By adopting the variable, isPKloop, it should be checked whether the loop is the PK loop or the regular loop. PK loop is different from the regular loop, so the radius and stem angle for the PK loop need to be independently calculated.

Figure 9:
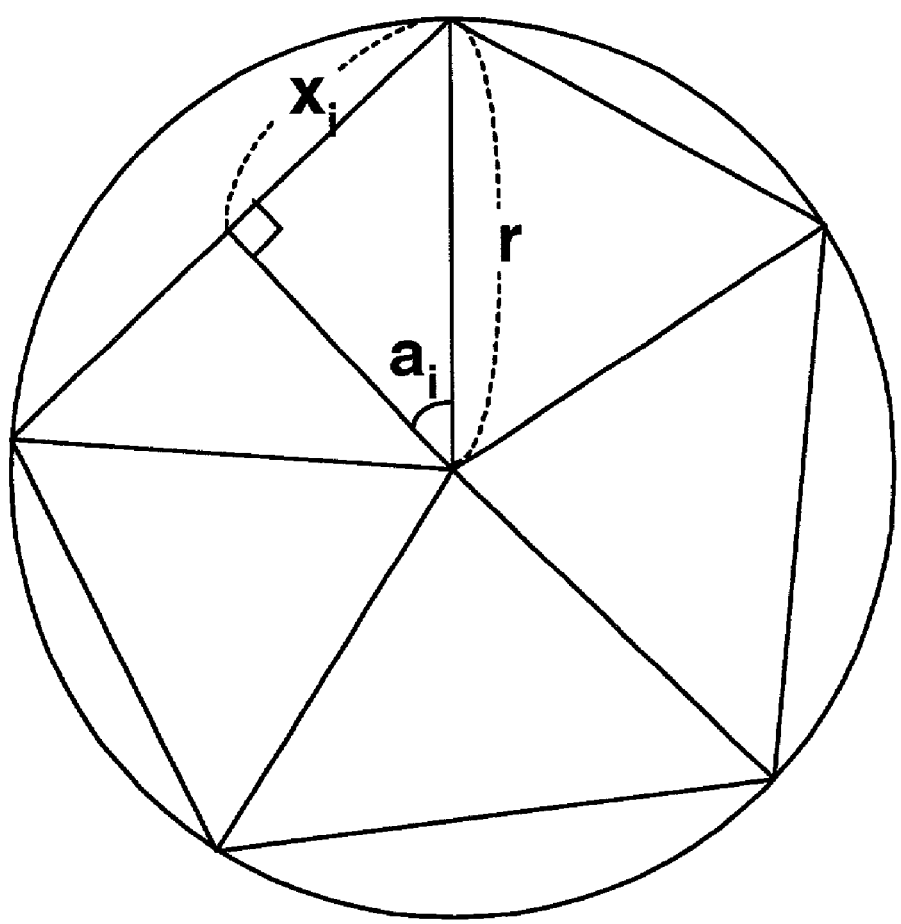
FIG. 9 is a drawing showing a radius of a pseudoknot loop.

To calculate the radius of the PK loop, several equations are available. Isosceles triangles are drawn by taking the positions of bases and the center as each vertex of the inscribed polygon of the PK loop (FIG. 9). Provided that the radius of the PK loop is r, and the angle and the length of the base side of each isosceles triangle is 2a and 2x, respectively. The following relation is obtained.

$$\sin(a_i) = \frac{x_i}{r} \Rightarrow a_i = \arcsin\left(\frac{x_i}{r}\right)$$ [Equation 8]

Further, providing that the number of isosceles triangles is n, Equation 9 is available.

$$\arcsin\left(\frac{x_1}{r}\right) + \arcsin\left(\frac{x_2}{r}\right) + \arcsin\left(\frac{x_3}{r}\right) + \ldots + \arcsin\left(\frac{x_n}{r}\right) = \pi$$ [Equation 9]

Equation 9 can be also expressed to a function of r, as shown in the equation below.

$$f = \sum_{i=1}^{n} \arcsin\left(\frac{x_i}{r}\right) - \pi = 0$$ [Equation 10]

Equation 10 is a monotonically decreasing function after a certain point. For the r value, Newton's method is not applied herein though the method is commonly used for numerical analysis, since the function f requires differentiation, complicating a differential result, thereby conferring a considerable computational complexity. For your reference, the differential equation is as in Equation 11.

$$\frac{df}{dr} = \sum_{i=1}^{n} \frac{-x_i}{r^2\sqrt{1 - \frac{x_i^2}{r^2}}} = \sum_{i=1}^{n} \frac{-x_i}{r\sqrt{r^2 - x_i^2}}$$ [Equation 11]

Instead of Newton's method, the radius r of the PK loop is determined by incrementing r value by a small step, thereby finding a point which is at a certain distance apart from zero.

Figure 10:
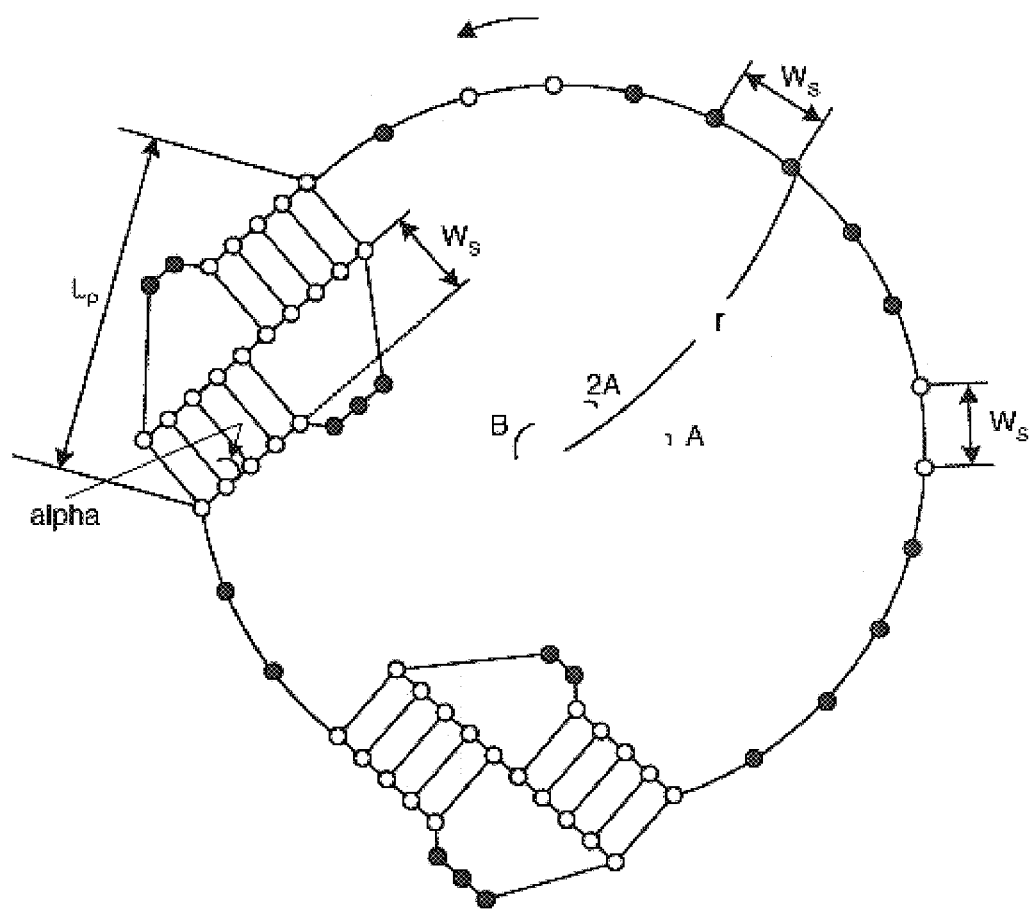
FIG. 10 is a drawing showing structural elements in a pseudoknot loop.
Figure 11:
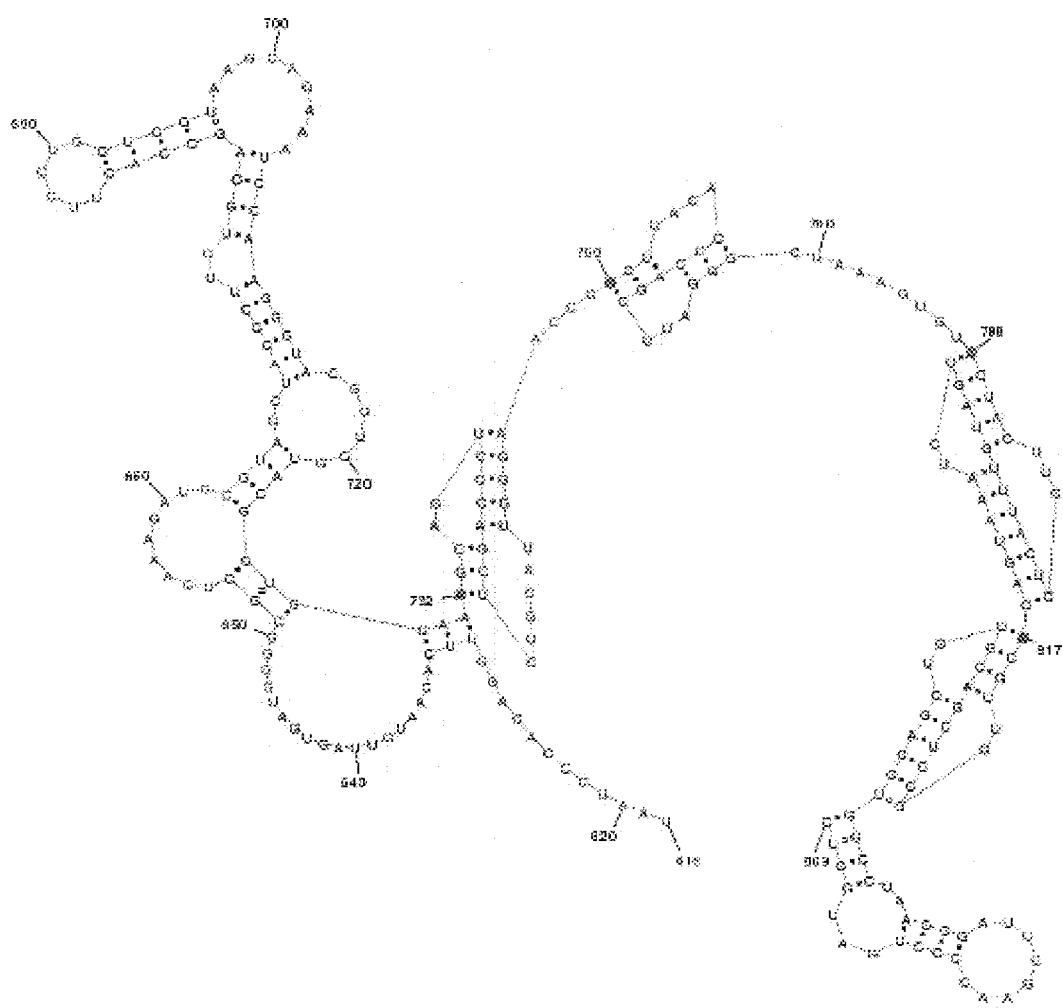
FIG. 11 is a drawing visualizing a RNA structure with 4 pseudoknots obtained from Satellite Tobacco Necrosis Virus-1 (STNV-1) (SEQ ID NO 2)
Figure 12:
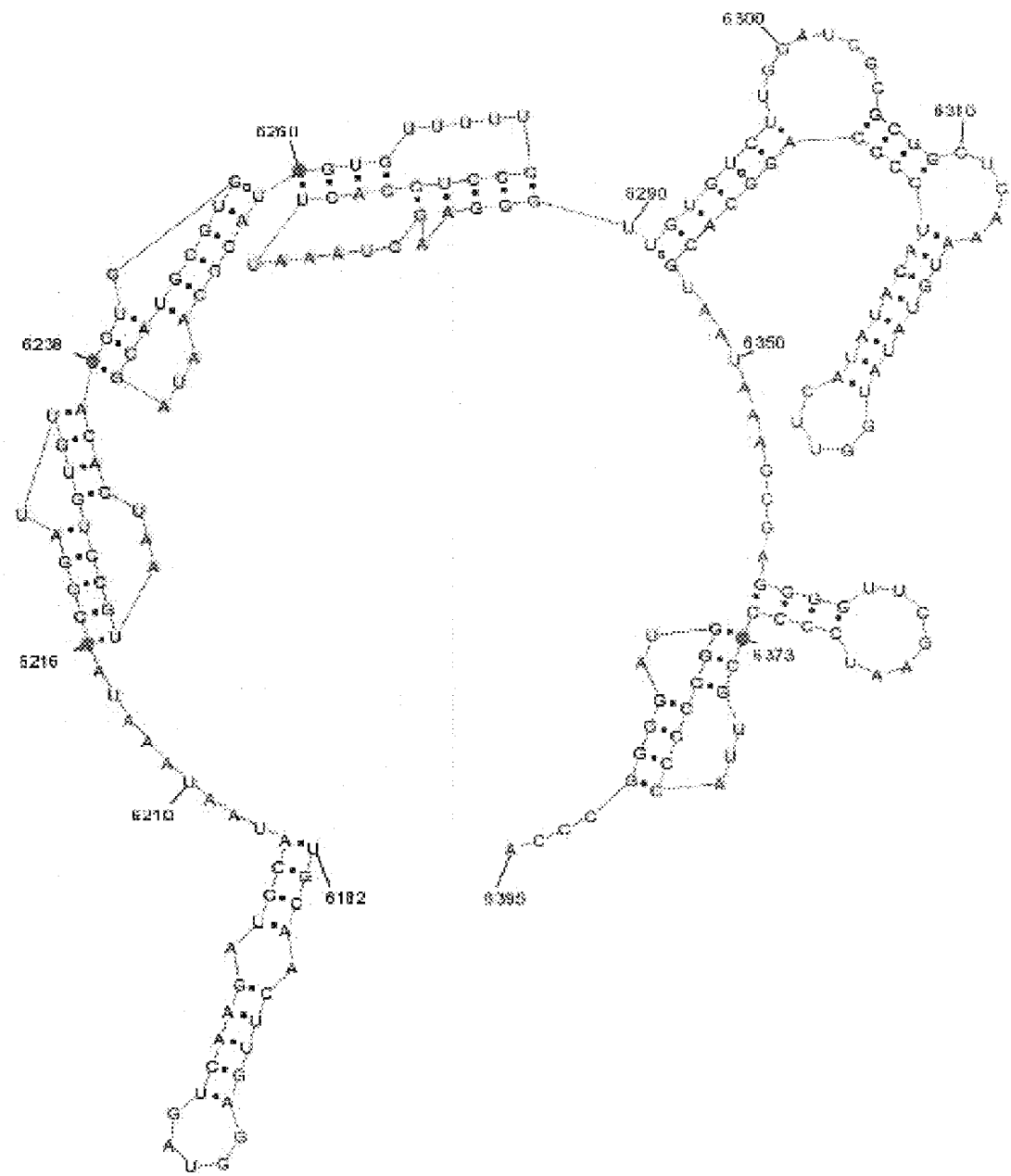
FIG. 12 is a drawing visualizing a RNA structure with 4 pseudoknots obtained from Tobacco Mosaic Virus (TMV) (SEQ ID NO 3)
Figure 13:
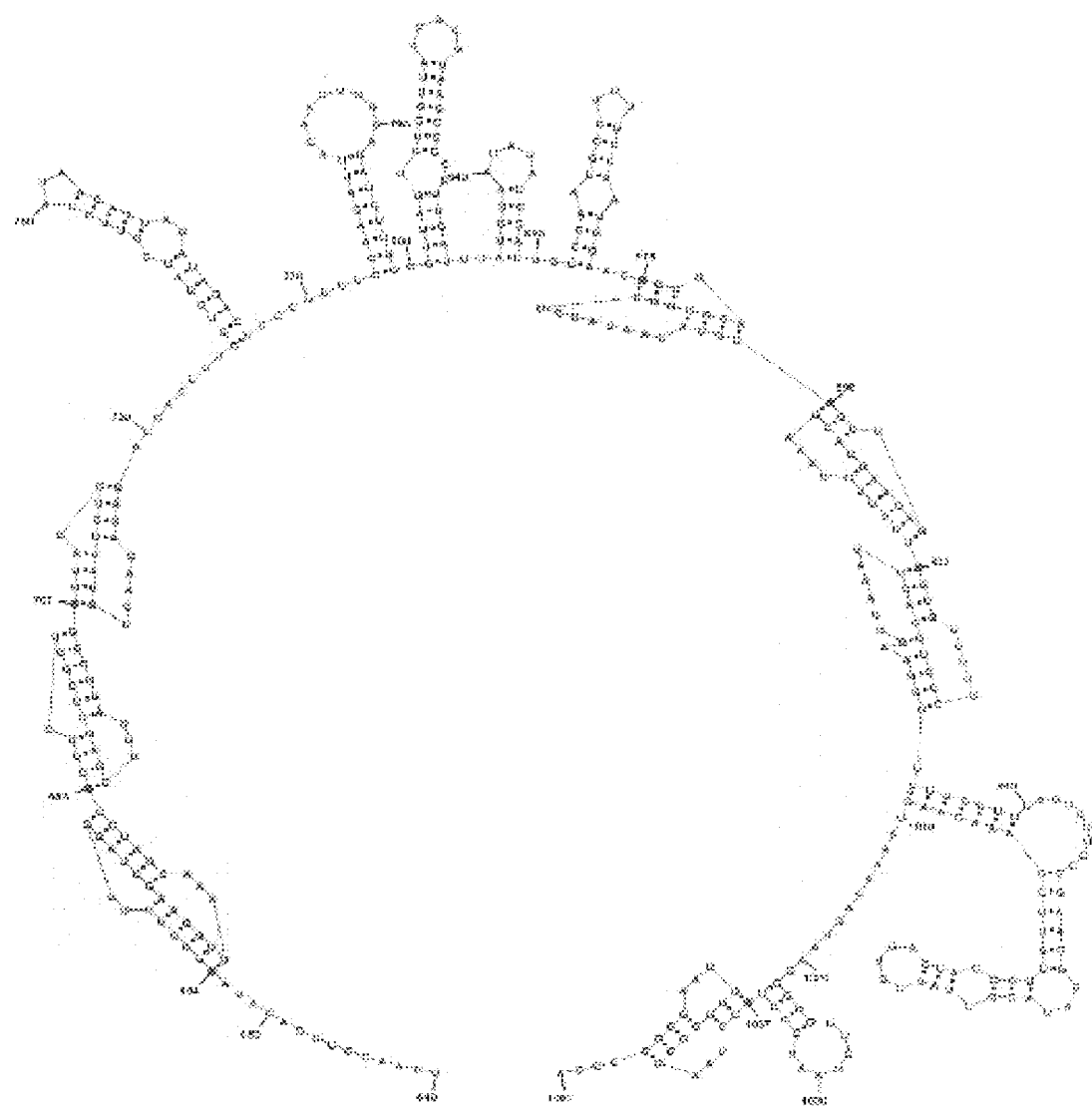
FIG. 13 is a drawing visualizing a RNA structure with 7 pseudoknots obtained from Satellite Tobacco Mosaic Virus (STMV) (SEQ ID NO 4)
Figure 14:
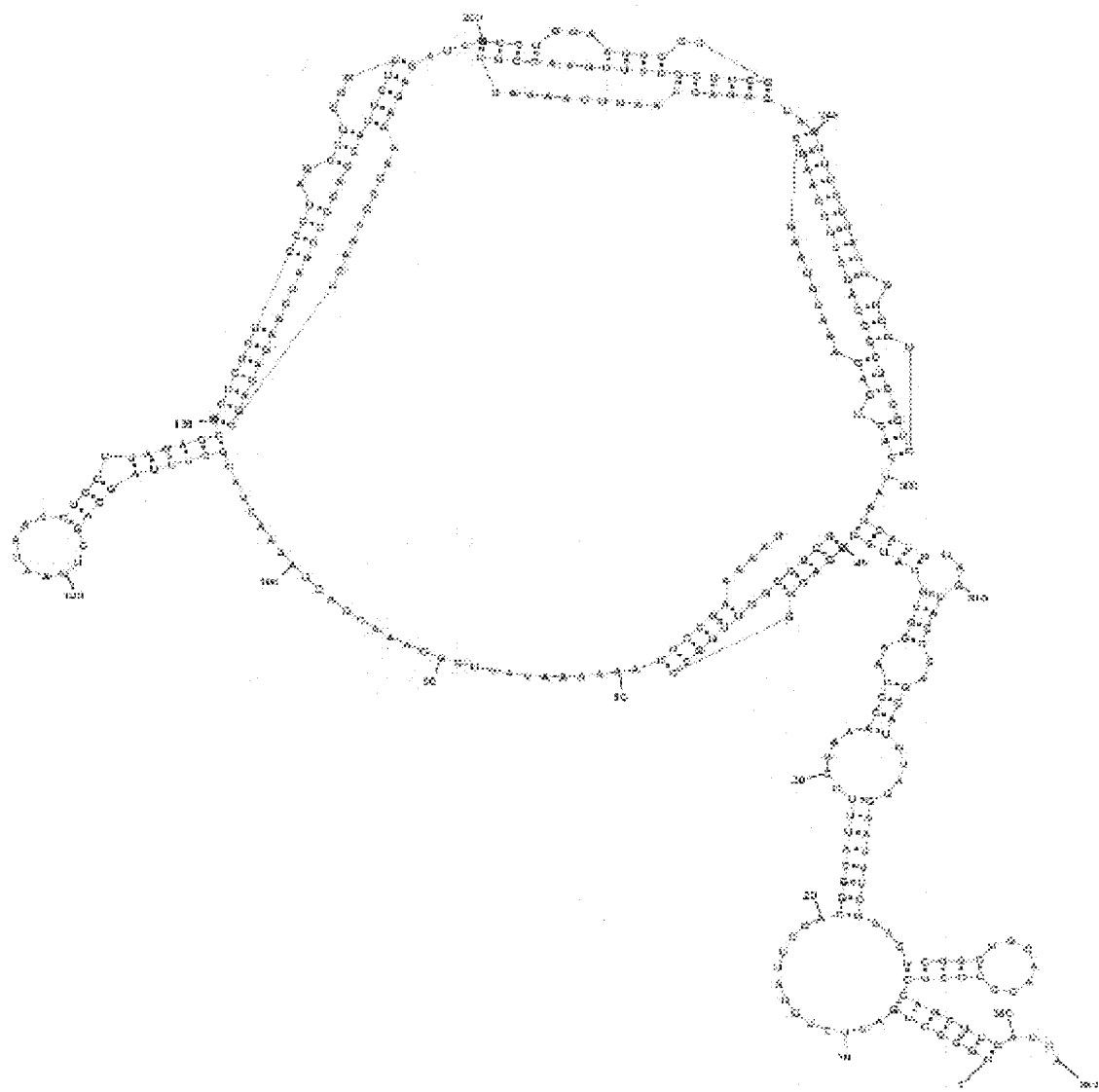
FIG. 14 is a drawing visualizing a tmRNA structure with 4 pseudoknots obtained from *E. coli* (SEQ ID NO 5); and, FIG. 15 is a drawing visualizing a RNA structure with 8 pseudoknots obtained from Odontoglossum Ringspot Virus (ORSV) (SEQ ID NO 6).
Figure 15:
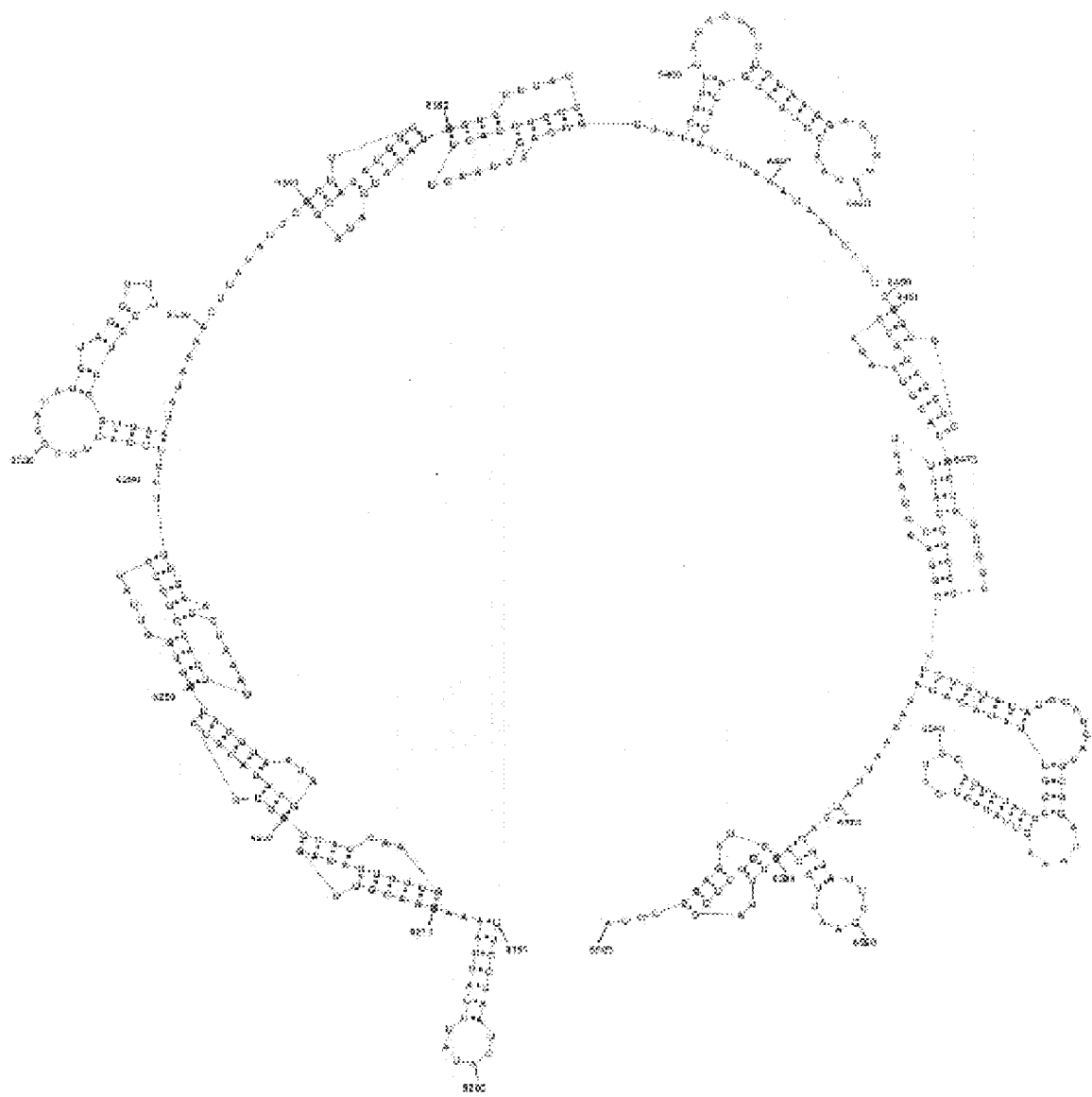

Once the radius r of the PK loop is determined, several angles associated with the PK loop can be calculated. Providing that the width of the stem, the distance between adjacent bases in the PK loop, the diagonal length (PKLength) of the bounding box for the pseudoknot are given, both the angle of the base which is not contained in the pseudoknot, with respect to a positive y-axis, and the angle between the starting base and the ending base in the pseudoknot can be calculated using Equation 12 and Equation 13, respectively (FIG. 10).

$$A = \arcsin\left(\frac{W_s}{2r}\right)$$ [Equation 12]

$$B = 2 \cdot \arcsin\left(\frac{L_p}{2r}\right)$$ [Equation 13]

In the above, $W_s$ represents the width of the stem (stemWidth) and also the distance between adjacent bases in the PK loop. $L_p$ represents the distance between the starting base and the ending base (the diagonal length of the pseudoknot region), and r represents the radius of the PK loop.

Positions of pseudoknots in the PK loop can be determined in a similar way as in the stem. Since the center and the startAngle of the PK loop are given in determining the entire structure of the PK loop, the coordinates of the starting bases in each pseudoknot can be calculated. In FIG. 10, alpha (α) represents the angle formed by the diagonal of the bounding box for the pseudoknot and the line parallel to the proceeding direction of the stem in the pseudoknot. For calculating the angle of the pseudoknot with respect to an y-axis, the pseudoknot should be oriented in the positive y-axis direction by rotating through an angle ω counterclockwise about its corner. The angle of the pseudoknot is the angle of the starting base in the pseudoknot added to 3Π/2.

$$\alpha = \arcsin\left(\frac{2W_s}{L_p}\right)$$ [Equation 14]

wherein, $W_s$ represents the width of the stem (stemWidth), and $L_p$ represents the diagonal length of the pseudoknot region.

Meanwhile, PseudoViewer is written in Java programming language, so it is executable on any type of computer flatform. FIGS. 11 to 15 show complicated RNA structures each containing multiple pseudoknots. In the drawings, bases in double-stranded parts are colored blue, while bases in single-stranded parts are colored red. Bases in pseudoknots are additionally background-colored yellow, thereby pseudoknots being easily distinguished from other structural elements. Along the PK loop, bases are numbered every 10 bases, but, in pseudoknot regions only the starting and ending bases are numbered. The bases of canonical pairs (A-U or G-C) are represented as blue filled circles and the bases of wobble pairs (G-U) as open circles.

As apparent from the above description, the visualization method of RNA pseudoknot structures of the invention is implemented using JAVA language, which is capable of being executed in a web-based modeling system. Based on the visualization of H-type pseudoknot structures, the improved implementation result is created with little effort and time for predicting and modeling RNA pseudoknot structures.

Through the implementation of the program, the complicated RNA structure containing many H-type pseudoknots can be visualized without edge crossings. Further, the implementation provides a clear and aesthetically pleasing drawing of the RNA structure without distortion of structural elements. It is different from manual drawings of pseudoknots in which a secondary structure is first drawn using a secondary structure-visualizing program, then the pseudoknots is added thereto with the aid of a graph-editing tool. The program according to the invention allows pseudoknot structures to be automatically visualized, thus being capable of serving as an efficient tool to users researching them.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A computer implemented method for predicting and modeling RNA pseudoknot structures, the method comprising the steps of: (a) setting criteria required for modeling RNA pseudoknots; (b) setting structural elements and data structures for representing a whole RNA structure containing pseudoknots; (c) determining an input format for modeling and a drawing order of the structure; (d) determining connectivity relations between regular loops and stems in the structure and between pseudoknot loops (PK loops) and stems in the structure; (e) calculating radii of the regular loops and the PK loops; (f) calculating coordinates of bases in the regular loops; (g) setting internal angles of the PK loops; (h) calculating startAngles of the regular loops and angles of the stems; (i) determining positions of the pseudoknots in the PK loops; and, (j) modeling by drawing the pseudoknots and the whole RNA structure containing the pseudoknots.

2. The method as set forth in claim 1, wherein the criteria in the step (a) include that overlapping of structural elements should be minimized to maximize the readability of the drawing.

3. The method as set forth in claim 1, wherein the structural elements in the step (b) comprise: a stem which denotes a double stranded part, containing two or more consecutive bases; a regular loop which denotes a single stranded part, containing non-pairing bases; a pseudoknot which denotes a tertiary structural element which is formed by pairing of bases in the regular loop with complementary bases outside the regular loop; and, a pseudoknot loop which denotes a loop containing another single stranded part as well as the pseudoknot.

4. The method as set forth in claim 3, wherein the regular loop includes hairpin loop, bulge loop, internal loop, multiple loop and dangling end.

5. The method as set forth in claim 3, wherein the structural elements further comprise a data member of baseVector, wherein said data member of baseVector is a variable of vector type.

6. The method as set forth in claim 1, wherein notations used for modeling a RNA pseudoknot include that all angles are measured with respect to the positive y-axis; that units of angles are radians rather than degrees; that Modulo Operator (%) is applied for calculating angle values since angle values should be in the range of [0, 2Π]; and, that bases are represented with different colors, according to whether bases pair with other bases or not.

7. The method as set forth in claim 1, wherein the determination of the input format for modeling and the sequence of drawing the structure in the step (c) comprises the steps of: c-1) determining coordinates of a starting point to draw a pseudoknot for input data, the pseudoknot including at least one stem having first and second base groups each including bases respectively paired with those of the other base group; c-2) determining a position of a last one of the bases included in the second base group of the stem in the pseudoknot by an x-coordinate value increased from the x-coordinate value of the starting point by a value corresponding to a stem width, and a y-coordinate value corresponding to the y-coordinate value of the starting point; c-3) determining respective positions of the remaining bases of the second base group in the stem in a reverse order by y-coordinate values sequentially incremented from the y-coordinate value of the starting point by the value corresponding to the stem width, and x-coordinate values each corresponding to the x-coordinate value of the last base of the second base group in the stem, so as to align the bases of the second base group in the stem along a center line extending in a y-axis direction while being spaced from the start point in an x-axis direction by the stem width; c-4) determining respective positions of the bases included in the first base group of the stem in a normal order by y-coordinate values respectively corresponding to the y-coordinate values of the associated bases of the second base group, and x-coordinate values each corresponding to the x-coordinate value of the starting point, so as to align the bases of the first base group in the stem along a line extending in a y-axis direction through the starting point; c-5) if there are bases included in a first base group of another stem between the first and second groups of the first one of the stems, determining respective positions of bases preceding the second base group of the first stem in a reverse order by y-coordinate values sequentially incremented from the y-coordinate value of the first base in the second base group of the first stem by the value corresponding to the stem width and x-coordinate values each corresponding to the x-coordinate value of the first base in the second base group of the first stem, until the position determination for a first one of bases in the first base group of the second stem is completed, so as to align the bases preceding the second base group of the first stem along the center line; c-6) if there are non-paired bases between the first base group of the first stem and the first base group of the second stem, determining respective positions of the non-paired bases in a normal order by y-coordinate values sequentially incremented from the y-coordinate value of the last base in the first base group of the first stem by the value corresponding to the stem width and an x-coordinate value reduced from the x-coordinate value of the starting point by the value corresponding to the stem width, so as to align the bases between the first base group of the second stem and the second base group of the first stem along a line extending in a y-axis direction while being spaced apart from the y-axis line extending through the start line, by the stem width; c-7) determining respective positions of bases included in the second group of the second stem in a normal order by y-coordinate values respectively corresponding to the y-coordinate values of the associated bases in the first base group of the second stem, and x-coordinate values respectively reduced from the x-coordinate values of the bases in the first base group of the second stem; and, c-8) if there are non-paired bases between the second base group of the first stem and the second base group of the second stem, determining respective positions of the non-paired bases preceding the second base group of the second stem in a reverse order by y-coordinate values sequentially decremented from the y-coordinate value of the first base in the second base group of the first stem by the value corresponding to the stem width and an x-coordinate value increased from the x-coordinate value of the first base in the second base group of the second stem by the value corresponding to the stem width, so as to align the non-paired bases preceding the second base group of the second stem along a line extending in a y-axis direction while being spaced from the center line by a distance double the stem width.

8. The method as set forth in claim 1, wherein the connectivity relation between regular loops and stems in the step (d) is one selected from the group consisting of: the case in which there is no intervening base between two stems, so one stem is directly adjacent to the other stem, the stems being connected to the loop; the case in which at least one intervening base is between two stems, the stems being connected to the loops; the case in which only one stem is connected to the loop; and, the case in which all stems connected to the loop are directly adjacent, with no intervening base between stems.

9. The method as set forth in claim 1, wherein the determination of connectivity relation between the regular loop and the stem in the step (d) comprises the steps of: d-1) determining whether or not a current base is an ending base of bases included in the stem, in which the regular loop starts from the determined ending base of the stem; d-2) determining the range of the regular loop by checking whether or not the current base has a non-pair value, in which where the current base has the non-pair value, it is a base of the regular loop; d-3) repeating the checking for all bases in the pseudoknot structure until the ending base of the regular loop is determined; d-4) searching the regular loop to find a starting base thereof only when "false" is assigned with regard to a value of isInRloop and a value of isInPKloop.

10. The method as set forth in claim 1, wherein the radius of the regular loop in step (e) is determined by $$r = \frac{x}{\sin a}$$

wherein:
x represents half of the distance between adjacent bases in the regular loop;
a represents the vertical angle a of the isosceles triangle, calculated by $$a = \frac{2\pi}{2n} = \frac{\pi}{n}$$

in which, n is the number of isosceles triangles formed in the regular loop, the isosceles triangles having a common vertex of the center of the loop and a same size, given that the distances between adjacent bases are the same.

11. The method as set forth in claim 1, wherein the xy coordinates of a base in the regular loop in the step (f) is determined by $x_i = -r \sin \theta_i + x_c$ and $y_i = r \cos \theta_i + y_c$, respectively wherein:
$x_i$ and $y_i$ represent, respectively, x and y coordinates of the $i^{th}$ base of the regular loop;
$x_c$ and $y_c$ represent, respectively, x and y coordinates of the center of the regular loop;
r represents the radius of the regular loop;
$\theta_i$ represents the angle between the $i^{th}$ base of the regular loop and the positive y-axis, calculated by $\theta_i = (2i+1)a$, i=0, 1, 2, ..., n−1, in which, a is the vertical angle of the isosceles triangle in the regular loop, being calculated by $$a = \arcsin\left(\frac{x}{r}\right),$$

where, if the number of intervening bases between adjacent stems which are connected to the regular loop is $n_b$, the angle δ between adjacent stems is calculated by $\delta = 2a(n_b+2)$, in which the angle between adjacent bases in the regular loop is equal to 2a.

12. The method as set forth in claim 1, wherein the startAngles of the regular loops and the angles of the stems in the step (h) are characterized by that where the regular loop has a loop level 0, both the angle of the first stem and the startAngle of the regular loop are zero, while the angle φ (stemAngle) of the stem other than the first stem is calculated by $\Phi = D_{loop} + \Pi + \delta$, wherein, $D_{loop}$ represents the startAngle of the upper regular loop;
δ represents the angle between adjacent stems in the regular loop;

in which, Π is added to make the stem having low-numbered bases point toward the upper regular loop, where, the startAngle of the lower regular loop is the same as the angle of the current stem.

13. The method as set forth in claim 1, further comprising the step of calculating the distance ($D_{rl}$) between regular loops, the distance being defined as the distance between the centers of two circles, each representing the regular loop, and is calculated by $D_{rl} = r_c + (n_{ub} - 1) \times h_s + r_u$ wherein:

$r_c$ represents the radius of the current regular loop;
$r_u$ represents the radius of the upper regular loop;
$n_{ub}$ represents the number of base pairs in the upper stem; and,
$h_s$ represents the distance between adjacent base pairs in the stem.

14. The method as set forth in claim 1, wherein the radius of the pseudoknot loop in the step (e) is determined by the function $$f = \sum_{i=1}^{n} \arcsin\left(\frac{x_i}{r}\right) - \pi = 0$$

wherein: r represents the radius of the pseudoknot loop,
where, the angle of the isosceles triangle is 2a and the length of the base side of the isosceles triangle is 2x, in which the isosceles triangles are drawn by taking the positions of bases and the center as each vertex in the pseudoknot loop, whereby, the equation $$\sin(a_i) = \frac{x_i}{r} \Rightarrow a_i = \arcsin\left(\frac{x_i}{r}\right)$$

is obtained; if the number of isosceles triangles is n, the equation $$\arcsin\left(\frac{x_1}{r}\right) + \arcsin\left(\frac{x_2}{r}\right) + \arcsin\left(\frac{x_3}{r}\right) + \cdots + \arcsin\left(\frac{x_n}{r}\right) = \pi$$

is obtained.

15. The method as set forth in claim 1, wherein the internal angles of the PK loop in the step (g) are the angle (A) of the base which is not contained in the pseudoknot, with respect to a positive y-axis, being calculated by $$A = \arcsin\left(\frac{W_s}{2r}\right),$$

and the angle (B) between an starting base and an ending base in the pseudoknot, being calculated by $$B = 2 \cdot \arcsin\left(\frac{L_p}{2r}\right)$$

wherein:
$W_s$ represents the width of the stem and also the distance between adjacent bases in the PK loop;
$L_p$ represents the distance between the starting base and the ending base (the diagonal length of bounding box for the pseudoknot region); and,
r represents the radius of the PK loop.

16. The method as set forth in claim 1, wherein the position of the pseudoknot within the PK loop in the step (i) is determined by calculating the coordinates of the starting bases in each pseudoknot and calculating the angle of the pseudoknot with respect to a y-axis, the pseudoknot being oriented in a positive y-axis direction by rotating through the angle ω counterclockwise about its corner, and being calculated by $$\alpha = \arcsin\left(\frac{2W_s}{L_p}\right),$$

wherein:
$W_s$ represents the width of the stem;
$L_p$ represents the diagonal length of the pseudoknot region; and,
α represents the angle formed by the diagonal of the bounding box for the pseudoknot and the line parallel to the proceeding direction of the stem in the pseudoknot,
where, the angle of the pseudoknot is the angle of the starting base in the pseudoknot added to 3Π/2.

17. The method as set forth in claim 1, wherein the computer implemented method comprises a program comprising a JAVA computer program language executable in an internet based platform.

* * * * *

SEQUENCE LISTING

<160> NUMBER OF SEQ ID NOS: 6

<210> SEQ ID NO 1
<211> LENGTH: 30
<212> TYPE: RNA
<213> ORGANISM: Escherichia coli

<400> SEQUENCE: 1 cgagggcgg uuggccucgu aaaaagccgc                                         30

<210> SEQ ID NO 2
<211> LENGTH: 252
<212> TYPE: RNA
<213> ORGANISM: Satellite Tobacco Necrosis Virus-1

<400> SEQUENCE: 2 uaauccccaga gguucacaau guuagugaug gggcgcugaa agaugcguag cuacccuucu        60
ggagccacuu ccuggguggua agcagaaauc caagggguacg guggggacggu ggaaagcagu     120 cccagcucug cauugggaac cggcuuacac ccagcuuagg gcuaaagugu acuacuugcu        180
cauuuguagu cuaaaugaga cguuggccuc gacgugucga ggguggccuaa gggauuggaa       240 ccccugaugg uc                                                           252

<210> SEQ ID NO 3
<211> LENGTH: 214
<212> TYPE: RNA
<213> ORGANISM: Tobacco Mosaic Virus

<400> SEQUENCE: 3
ugcaacuuga gguagucaag augcauaaua aauaacggau ugugugccgua aucacacgug        60 gugcguacga uaacgcauag guuuuuuccc uccacuuaaa ucgaagggguu gugucuugga      120 ucgcgcgggu caaauguaua ugguucauau acauccgcag gcacguaaua aagcgagggg       180
uucgaauccc cccguuaccc ccgguagggg ccca                                   214

<210> SEQ ID NO 4
<211> LENGTH: 421
<212> TYPE: RNA
<213> ORGANISM: Satellite Tobacco Mosaic Virus

<400> SEQUENCE: 4
ugaaccucga cauaagccuu uuggaucgaa gguuaaacga uccgcuccuc gcuugagcuu        60
gaggcggcgu aucucuuaug ucaacagaga ccacuuuggu cuauguugu auaacaauag       120 auagacuccc guuugcaaga uuacaauugg gagaucuugc cguuagucug guuagcgcgu      180
aaccggccuu gauuuaugga auagauccau ugccaauugg cuuugccaau ggaacgccga      240
cguggcugua uaauacgucg uugacaagua cgaaaucuug uuaguguuuu ucccuccacu      300
uaaaucgaag gguuuuguuu uggucuuccc gaacgcauac guuaguguga cuaccguugu      360
ucgaaacaag uaaaacagga aggggguucg aaucccuccc uaaccgcggg uaagcggccc      420
a                                                                     421

<210> SEQ ID NO 5
<211> LENGTH: 363
<212> TYPE: RNA
<213> ORGANISM: Escherichia coli

<400> SEQUENCE: 5

-continued

```
gggcugauu cuggauucca cgggauuugc gaaacccaag gugcaugccg aggggcgguu      60
ggccucguaa aaagccgcaa aaaauagucg caaacgacga aaacuacgcu uuagcagcuu    120
aauaaccugc uuagagcccu cucucccuag ccuccgcucu uaggacgggg aucaagagag    180
gucaaaccca aaagagaucg cguggaagcc cugccugggg uugaagcguu aaaacuuaau    240
caggcuaguu uguuagugge guguccgucc gcagcuggca agcgaaugua aagacugacu    300
aagcauguag uaccgaggau guaggaauuu cggacgcggg ugcaacgccc gccagcucca    360
cca                                                                 363

<210> SEQ ID NO 6
<211> LENGTH: 419
<212> TYPE: RNA
<213> ORGANISM: Odontoglossum Ringspot Virus

<400> SEQUENCE: 6
uuccuaauca uauuuaggaa aauaacguug auaguguuga acuauccgug gugcauacga     60
uaaugcauag ugguuauccc uccacuuaaa ucgaaggguu uuucacugcg gauauguagg    120
uuuccucggu gaauauaaaa cuuauauccc guuguguaca cgauaguaca uaguguuuau    180
cccuccacuu gaaucgaagg guuuuguguc agacgcgugu aaggaguggu caaccuuacg    240
acacauuuaa auaaugcguc cguggugcau acgauaaugc auaguguuug ucccuccacu    300
uaaaucgaag gguuguguau auggaucaug cggauaaagu uauacuggug caguauaacc    360
cguuauacac auaaaauuau gagggauucg aauuccccu uaccucgggu agaggccca     419
```